(12) United States Patent
McLaughlin

(10) Patent No.: US 6,923,991 B2
(45) Date of Patent: Aug. 2, 2005

(54) BACTERICIDE SOLUTION AND METHOD OF MAKING SAME

(75) Inventor: Francis Benjamin McLaughlin, Bloomfield, MI (US)

(73) Assignee: Global Microbio Products, L.L.C., Farmington Hills, MI (US)

( * ) Notice: Subject to any disclaimer, the term of this patent is extended or adjusted under 35 U.S.C. 154(b) by 0 days.

(21) Appl. No.: 10/369,384

(22) Filed: Feb. 19, 2003

(65) Prior Publication Data

US 2003/0157188 A1 Aug. 21, 2003

Related U.S. Application Data

(60) Provisional application No. 60/357,968, filed on Feb. 20, 2002, and provisional application No. 60/362,331, filed on Mar. 8, 2002.

(51) Int. Cl.$^7$ .......................... A01N 59/02; A01N 59/20
(52) U.S. Cl. ...................... 424/637; 424/630; 424/638; 424/703; 504/151; 504/152; 426/335; 426/532
(58) Field of Search ................................. 424/630, 637, 424/638, 703, 601, 605, 616, 666, 708; 504/151, 152; 426/335, 532; 514/557–560

(56) References Cited

U.S. PATENT DOCUMENTS 5,780,064 A * 7/1998 Meisters et al. ............ 424/616

OTHER PUBLICATIONS

Derwent Abstract, accession No. 1997–386146, abstracting CN 1111092 (Nov. 1995).*
Chemical Abstracts 124:253334, abstracting CN 1111092 (Nov. 1995).*
The Merck Index, 12$^{th}$ ed., Merck & Co. Inc., Whitehouse Station, NJ, 1996, p. 447.*

* cited by examiner

Primary Examiner—John Pak
(74) Attorney, Agent, or Firm—Reising, Ethington, Barnes, Kisselle, P.C.

(57) ABSTRACT

A bactericide useful as a shelf life extender for produce and other food products. The bactericide is an aqueous solution formed from water, copper sulfate pentahydrate and a reagent, which can either be an acid or hydrogen peroxide. The bactericide is applied as a coating on the food product and is especially useful in extending the shelf life of fruits and vegetables. Other applications of the bactericide include treatment of drinking water, bacteria and algae control in pools and natural bodies of, water and as a disinfectant in cleansers.

4 Claims, No Drawings

BACTERICIDE SOLUTION AND METHOD OF MAKING SAME

CROSS-REFERENCE TO RELATED APPLICATIONS

This application claims the benefit of U.S. Provisional application No. 60/357,968, filed Feb. 20, 2002, and U.S. Provisional application No. 60/362,331, filed Mar. 8, 2002. The entire contents of these two provisional applications are hereby incorporated by reference.

TECHNICAL FIELD

This invention relates generally to bactericides and especially to bactericide solutions applied to fruits, vegetables, and other food products to extend their shelf life.

BACKGROUND OF THE INVENTION

Food products for human and other animal consumption typically have only a limited shelf life; meaning that they become spoiled or otherwise loose their appeal or nutritional value after a period of time. This shelf life varies with different parameters of the food product including the particular type of food involved and the temperature at which it is maintained. This limited shelf life is the result of microbiological processes that occur to break down the food over time.

Limited shelf life can have a tremendous impact on the food distribution chain from the farmer or manufacturer, through the distributors and retail grocers, all the way to the end consumer. For produce such as fruits and vegetables, their normally short shelf life may require time-critical management of the produce by the various players in the food distribution chain. For example, farmers may need to carefully time their harvesting and transportation. Distributors may have to maintain large, yet short term inventory levels, and the grocers ultimately have to maintain a high turnover rate of these food items while providing a consistent supply for its consumers. Interspersed between all of these players is a need for regular, reliable delivery of the food products.

Various approaches have been used to extend the shelf life of such products. This includes refrigeration, the use of preservatives, and shelf life extenders. In the case of fruits and vegetables, shelf life extenders typically comprise a liquid solution that may be sprayed onto or otherwise coated over the food product.

SUMMARY OF THE INVENTION

The present invention provides a shelf life extender for produce and other food products that can be applied as a coating by any suitable means such as spraying or dip coating. The shelf life extender is made by adding copper sulfate pentahydrate to an aqueous solution and thereafter mixing a quantity of reagent into the solution. The reagent is selected from the group consisting of an acid and hydrogen peroxide. In one preferred embodiment, sulfuric acid is used. The order of the steps can be reversed, and the resulting solution can be diluted in concentration depending upon the intended application.

In accordance with another aspect of the present invention, the solution can be used as a bactericide useful for destroying pathogenic bacteria and fungi. Applications of the solution as a bactericide include treatment of drinking water, bacteria and algae control in pools and natural bodies of water, and as a disinfectant in cleansers.

DETAILED DESCRIPTION OF THE PREFERRED EMBODIMENTS

The following description of the bactericide and shelf life extender of the present invention will be of preferred embodiments and in amounts suitable for its use. However, it is to be understood that the embodiments and volumetric amounts discussed herein are exemplary only and the actual scope of the invention is limited only by the appended claims.

In general, the bactericide is an aqueous solution of copper sulfate and a reagent which together provide an antibacterial effect that in proper concentrations is not harmful to humans and other animals. The copper sulfate is primarily in the form of copper sulfate pentahydrate, and the reagent can either be a suitable acid or a strong base such as hydrogen peroxide.

In accordance with a specific embodiment of the invention, the bactericide can be made by slowly adding 200 grams of crystalline copper sulfate pentahydrate ($CuSO_4.5H_2O$) to about 500 ml of water in a liter flask. The water is preferably distilled, deionized, or tap water such as is available from a municipal potable water supply. Other water (e.g., hard water) can be used depending upon the intended application, but is not preferred since it may contain elevated sodium, calcium, iron, manganese, and other minerals. This aqueous solution is stirred using, for example, a magnetic stirring bar until the copper sulfate has complete dissolved. With continued stirring, about 60 ml of sulfuric acid is added and the resulting solution is then allowed to cool. Thereafter, a quantity sufficient of water is added to the resulting solution to bring it to a total of one liter. This solution comprises a concentrated stock solution of the bactericide. A concentrated stock solution of the bactericide can also be prepared by (1) dissolving copper sulfate petahydrate in a volume of water to a concentration of from about 40 w/v % copper sulfate pentahydrate to a fully saturated solution of copper sulfate pentahydrate; and (2) mixing a volume of sulfuric acid into the solution obtained in step (1), wherein the concentration of sulfuric acid in the volume of water is about 1:50 to about 9:50. Various working solutions for use as a shelf life extender or for other applications can be made from this stock solution by diluting it with water, and the amount of water will depend on the particular application, as will be described in further detail below.

The copper sulfate pentahydrate can be added in concentrations other than that noted above. In particular, it can be added to water to form a resulting concentration that is as little as 1% or as great as a fully saturated solution in which no further crystals can be dissolved. The amount of sulfuric acid reagent can also be varied. It may be added to form as little as 1% of acid to solution or as much as 90% of the solution. In a more preferred embodiment, the amount used is between 2% and 18% so that, in the specific example described above using 200 grams of copper sulfate pentahydrate and 500 ml of water, the amount of sulfuric acid can be varied within this range from 10 ml to 90 ml.

The sulfuric acid is but one of a number of different reagents that can be used. In general, a variety of different acids can be used as the reagent, including sulfuric acid, hydrochloric acid, nitric acid, and phosphoric acid. Alternatively, hydrogen peroxide can be used as the reagent in addition to or in lieu of one or more acids, in which case it can be used in diluted or concentrated form, anywhere from 1% to 100%. Combinations of two or more acids can be used as well, including combinations with acids not listed above. Where multiple reagents are used, they can be first combined together, or individually added sequentially or simultaneously.

Rather than dissolving the copper sulfate pentahydrate first and then adding the reagent, the reagent can first be diluted to the desired amount in water, followed by the addition of the copper sulfate pentahydrate to the diluted reagent.

Once the stock solution is prepared using any of the variations noted above, it is ready for use. The stock solution can be used directly, but preferably will be in a concentrated form that would be diluted for most applications, particularly where it is applied to fruits or vegetables. For example, it has been determined that using the specific example given above with the specific amounts of copper sulfate pentahydrate and reagent, that a working solution for fruits and vegetables can be made by diluting one part stock solution to about fifteen thousand parts water. Again, the water is preferably distilled, deionized, or tap. This yields 4 mg/liter (4 parts per million) of the shelf life extender. Even more preferred for such a working solution is to dilute four parts of the stock solution to 59,400 parts water. Again, this is a specific concentration that has been found to provide good balance between cost and efficacy for use on produce. Other concentrations for use with produce can be used, and the working solution for such an application is preferably within the range of one part per million to one hundred parts per million. In a more preferred embodiment, the range of concentrations is from three parts per million to five parts per million.

The shelf life extender can be applied by spraying, dip coating, or any other suitable means. When used for produce, the prepared solution can be placed into a vat with the produce being put into a sieve basket that is then immersed into the vat of solution. The basket is immediately withdrawn after being immersed into the solution and allowed to drain back into the vat. Preferably, plastic-type baskets are used rather than metal or wood. In this regard, the solution is preferably not stored or used in any type of metal container, and is preferably kept from freezing.

The efficacy of the solution has been demonstrated empirically through testing, with produce enjoying an extended shelf life of anywhere between 34% and 125% versus untreated produce, depending upon the type of produce involved.

Apart from its use to maintain freshness of produce and other foodstuffs, the solution can be used for other purposes as well. For example, in concentrations from 1 mg to 1.3 mg per liter of water it can be used for water treatment (bottled water and other potable water sources, as well as in ice making). In concentrations of 4 mg to 10 mg per liter it can be added to pools and lakes to control algae and bacteria. In concentrations of 8 mg to 20 mg per liter it can be used as an additive to engine coolant to control the colonization of promulgation of organisms found in coolant. For poultry processing, it can be used in concentrations of 4 mg to 10 mg per liter for drinking water to protect poultry from *Salmonella, Lysteria, Monocytogenes*, and *Campylobacter*. It can also be used as a spray for poultry environmental areas in a concentration of 10 mg to 20 mg. As a bactericide, it can be used in concentrations of 4 mg to 8 mg as a disinfectant cleanser for food preparation areas and incorporated into a soap base for topical use in hand washing.

It will thus be apparent that there has been provided in accordance with the present invention a bactericide and shelf life extender which achieves the aims and advantages specified herein. It will of course be understood that the foregoing description is of preferred exemplary embodiments of the invention and that the invention is not limited to the specific embodiments shown. Various changes and modifications will become apparent to those skilled in the art and all such variations and modifications are intended to come within the scope of the appended claims.

What is claimed is:

1. A method of preparing a bactericide, comprising the steps of:

adding copper sulfate pentahydrate to an aqueous solution; and mixing a quantity of sulfuric acid into the solution;

wherein said adding step comprises dissolving about 200 grams of copper sulfate pentahydrate to about 500 ml of water, and said mixing step comprises mixing about 60 ml of sulfuric acid into the solution of dissolved copper sulfate pentahydrate.

2. The method of claim 1, wherein said mixing step produces a concentrated stock solution, and wherein the method further comprises the step of diluting the stock solution with water.

3. A method of preparing a bactericide, comprising the steps of:

(1) dissolving copper sulfate pentahydrate in a volume of water to a concentration of from about 40 w/v % copper sulfate pentahydrate to a fully saturated solution of copper sulfate pentahydrate; and (2) mixing a volume of sulfuric acid into the solution obtained in step (1), wherein the concentration of sulfuric acid in the volume of water is about 1:50 to about 9:50.

4. The method of claim 3, wherein the solution obtained in step (2) is a concentrated stock solution, and wherein the method further comprises the step of diluting the stock solution with water.

* * * * *